US009199892B2

(12) United States Patent
Vincent et al.

(10) Patent No.: US 9,199,892 B2
(45) Date of Patent: Dec. 1, 2015

(54) ALKYLATION PROCESS

(71) Applicant: BADGER LICENSING LLC, Boston, MA (US)

(72) Inventors: Matthew J. Vincent, Kingwood, TX (US); Vijay Nanda, Houston, TX (US); Brian Maerz, Chelmsford, MA (US); Maruti Bhandarkar, Kingwood, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 13/746,965

(22) Filed: Jan. 22, 2013

(65) Prior Publication Data

US 2013/0137910 A1    May 30, 2013

Related U.S. Application Data

(63) Continuation-in-part of application No. PCT/US2011/044371, filed on Jul. 18, 2011.

(60) Provisional application No. 61/378,262, filed on Aug. 30, 2010.

(30) Foreign Application Priority Data

Oct. 28, 2010    (EP) ..................................... 10189234

(51) Int. Cl.
*C07C 2/66* (2006.01)
*C10G 29/20* (2006.01)

(52) U.S. Cl.
CPC ................ *C07C 2/66* (2013.01); *C10G 29/205* (2013.01); *C07C 2529/08* (2013.01); *C07C 2529/70* (2013.01); *C10G 2300/1044* (2013.01); *C10G 2300/1092* (2013.01); *C10G 2300/1096* (2013.01); *C10G 2300/4006* (2013.01); *C10G 2300/4012* (2013.01); *C10G 2300/4018* (2013.01); *C10G 2400/30* (2013.01)

(58) Field of Classification Search
USPC ....................................................... 585/467
See application file for complete search history.

(56) References Cited

U.S. PATENT DOCUMENTS

| 3,293,192 | A | 12/1966 | Maher et al. |
| 3,308,069 | A | 3/1967 | Wadlinger et al. |
| 3,354,078 | A | 11/1967 | Miale et al. |
| 3,442,795 | A | 5/1969 | Kerr et al. |
| 3,449,070 | A | 6/1969 | McDaniel et al. |
| 3,751,504 | A | 8/1973 | Keown et al. |
| 4,016,218 | A | 4/1977 | Haag et al. |
| 4,362,697 | A | 12/1982 | Tabb et al. |
| 4,415,438 | A | 11/1983 | Dean et al. |
| 4,429,176 | A | 1/1984 | Chester et al. |
| 4,439,409 | A | 3/1984 | Puppe et al. |
| 4,459,426 | A | 7/1984 | Inwood |
| 4,522,929 | A | 6/1985 | Chester et al. |
| 4,547,605 | A | 10/1985 | Kresge et al. |
| 4,594,146 | A | 6/1986 | Chester et al. |
| 4,663,492 | A | 5/1987 | Chester et al. |
| 4,826,667 | A | 5/1989 | Zones et al. |
| 4,891,458 | A | 1/1990 | Innes et al. |
| 4,954,325 | A | 9/1990 | Rubin et al. |
| 4,992,606 | A | 2/1991 | Kushnerick et al. |
| 5,003,119 | A | 3/1991 | Sardina et al. |
| 5,236,575 | A | 8/1993 | Bennett et al. |
| 5,250,277 | A | 10/1993 | Kresge et al. |
| 5,334,795 | A | 8/1994 | Chu et al. |
| 5,557,024 | A | 9/1996 | Cheng et al. |
| 5,600,048 | A | 2/1997 | Cheng et al. |
| 5,600,050 | A | 2/1997 | Huang et al. |
| 5,959,168 | A | 9/1999 | Van der Aalst et al. |
| 6,077,498 | A | 6/2000 | Diaz Cabanas et al. |
| 6,231,751 | B1 | 5/2001 | Canos et al. |
| 6,376,730 | B1 | 4/2002 | Jan et al. |
| 6,756,030 | B1 | 6/2004 | Rohde et al. |
| 6,888,037 | B2 * | 5/2005 | Dandekar et al. ............. 585/467 |
| 6,984,764 | B1 | 1/2006 | Roth et al. |
| 6,995,295 | B2 | 2/2006 | Clark et al. |
| 7,411,101 | B2 | 8/2008 | Chen et al. |
| 7,425,659 | B2 * | 9/2008 | Clark ............................ 585/467 |
| 7,645,913 | B2 | 1/2010 | Clark et al. |
| 7,649,122 | B2 | 1/2010 | Clark et al. |
| 7,713,513 | B2 | 5/2010 | Jan et al. |
| 2002/0137977 | A1 | 9/2002 | Hendriksen et al. |
| 2004/0138051 | A1 | 7/2004 | Shan et al. |
| 2005/0197517 | A1 | 9/2005 | Cheng et al. |

(Continued)

FOREIGN PATENT DOCUMENTS

| EP | 0 293 032 | 11/1988 |
| EP | 0 847 802 | 6/1998 |
| WO | WO 97/17290 | 5/1997 |
| WO | WO 2005/118476 | 12/2005 |
| WO | WO 2006/002805 | 1/2006 |
| WO | WO 2006/107471 | 10/2006 |

OTHER PUBLICATIONS

Miale et al., "*Catalysis by Crystalline Aluminosilicates IV. Attainable Catalytic Cracking Rate Constants, and Superactivity*", Journal of Catalysis, vol. 6, pp. 278-287 (1966).
Olson et al., "*Chemical and Physical Properties of the ZSM-5 Substitutional Series*", Journal of Catalysis, vol. 61, pp. 390-396 (1980).
Weisz, "*Superactive Crystalline Aluminosilicate Hydrocarbon Catalysts*", Journal of Catalysis, vol. 4, pp. 527-529 (1965).

*Primary Examiner* — Thuan D Dang
(74) *Attorney, Agent, or Firm* — Darryl M. Tyus

(57) ABSTRACT

The present invention provides an improved process for the catalytic conversion of a feedstock comprising an alkylatable aromatic compound and an alkylating agent to form a conversion product comprising the desired alkylaromatic compound by contacting said feedstock in at least partial liquid phase under catalytic conversion conditions with a catalyst composition comprising a porous crystalline material having a structure type of FAU, BEA* or MWW, or a mixture thereof, wherein the porous crystalline material has a Relative Activity measured at 220° C. as an $RA_{220}$ of at least 7.5 or measured at 180° C. as $RA_{180}$ of at least 2.5, allowing operation at lower reaction pressures, e.g., a reaction pressure of about 450 psig (3102 kPa) or less, and lower alkylating agent feed supply pressure of 450 psig (3102 kPa) or less.

4 Claims, No Drawings

(56) References Cited

U.S. PATENT DOCUMENTS

| | | |
|---|---|---|
| 2006/0247480 A1 | 11/2006 | Jan et al. |
| 2008/0287720 A1 | 11/2008 | Clark |
| 2008/0319242 A1 * | 12/2008 | Clark et al. .................. 585/447 |
| 2009/0112028 A1 | 4/2009 | Schultz |
| 2009/0137855 A1 | 5/2009 | Clark et al. |
| 2009/0234169 A1 | 9/2009 | Pelati et al. |

* cited by examiner

ALKYLATION PROCESS

PRIORITY CLAIM

This application is a continuation-in-part of International Application No. PCT/US2011/044371 filed Jul. 18, 2011, which claims the benefit of and priority to U.S. Provisional Application Ser. No. 61/378,262 filed Aug. 30, 2010 and which claims priority to European Application No. 10189234.7 filed Oct. 28, 2010, the disclosures of which are fully incorporated herein in their entireties by reference.

BACKGROUND OF THE INVENTION

The present invention relates to an improved process for producing alkylaromatics such as ethylbenzene and cumene.

Of the alkylaromatic compounds advantageously produced by the present improved process, ethylbenzene and cumene, for example, are valuable commodity chemicals which are used industrially for the production of styrene monomer and coproduction of phenol and acetone respectively. In fact, a common route for the production of phenol comprises a process which involves alkylation of benzene with propylene to produce cumene, followed by oxidation of the cumene to the corresponding hydroperoxide, and then cleavage of the hydroperoxide to produce equimolar amounts of phenol and acetone. Ethylbenzene may be produced by a number of different chemical processes. One process which has achieved a significant degree of commercial success is vapor phase alkylation of benzene with ethylene in the presence of a solid, acidic ZSM-5 zeolite catalyst. Examples of such ethylbenzene production processes are described in U.S. Pat. No. 3,751,504 (Keown), U.S. Pat. No. 4,547,605 (Kresge) and U.S. Pat. No. 4,016,218 (Haag). U.S. Pat. No. 5,003,119 (Sardina) describes the use of zeolite X, zeolite Y, zeolite L, zeolite Beta, ZSM-5, zeolite Omega, and mordenite and chabazite in synthesis of ethylbenzene. U.S. Pat. No. 5,959,168 (van der Aalst) describes the use of zeolite Y, zeolite Beta, MCM-22, MCM-36, MCM-49 and MCM-56 in synthesis of ethylbenzene in a plant designed for use of aluminum chloride-based catalyst.

Another process which has achieved significant commercial success is liquid phase alkylation for producing ethylbenzene from benzene and ethylene since it operates at a lower temperature than the vapor phase counterpart and hence tends to result in lower yields of by-products. For example, U.S. Pat. No. 4,891,458 (Innes) describes the liquid phase synthesis of ethylbenzene with zeolite Beta, whereas U.S. Pat. No. 5,334,795 (Chu) describes the use of MCM-22 in the liquid phase synthesis of ethylbenzene; and U.S. Pat. No. 7,649,122 (Clark) describes the use of MCM-22 in the liquid phase synthesis of ethylbenzene in the presence of a maintained water content. U.S. Pat. No. 4,459,426 (Inwood) describes the liquid phase synthesis of alkylbenzene with steam stabilized zeolite Y. U.S. Patent Publication No. 2009/0234169 A1 (Pelati) describes the liquid phase aromatic alkylation over at least one catalyst bed containing a first catalyst modified by inclusion of a rare earth metal ion.

Cumene has been produced commercially by the liquid phase alkylation of benzene with propylene over a Friedel-Craft catalyst, particularly solid phosphoric acid or aluminum chloride. Zeolite-based catalyst systems have been found to be more active and selective for propylation of benzene to cumene. For example, U.S. Pat. No. 4,992,606 (Kushnerick) describes the use of MCM-22 in the liquid phase alkylation of benzene with propylene.

Other Publications show use of catalysts comprising crystalline zeolites for conversion of feedstock comprising an alkylatable aromatic compound and an alkylating agent to alkylaromatic conversion product under at least partial liquid phase conversion conditions. These include U.S. 2005/0197517A1 (Cheng); U.S. 2002/0137977A1 (Hendrickson); and U.S. 2004/0138051A1 (Shan) showing use of a catalyst comprising a microporous zeolite embedded in a mesoporous support; WO 2006/002805 (Spano); and U.S. Pat. No. 6,376,730 (Jan) showing use of layered catalyst; EP 0847802B1; and U.S. Pat. No. 5,600,050 (Huang) showing use of catalyst comprising 30 to 70 wt. % H-Beta zeolite, 0.5 to 10 wt. % halogen, and the remainder alumina binder.

Other such Publications include U.S. Pat. No. 5,600,048 (Cheng) describing preparing ethylbenzene by liquid phase alkylation over acidic solid oxide such as MCM-22, MCM-49 and MCM-56, zeolite Beta, zeolite X, zeolite Y or mordenite; U.S. Pat. No. 7,411,101 (Chen) describing preparing ethylbenzene or cumene by liquid phase alkylation over acidic solid oxide such as PSH-3, ITQ-2, MCM-22, MCM-36, MCM-49, MCM-56, and zeolite Beta at conversion conditions including a temperature as high as 482° C. and pressure as high as 13,788 kPa; and U.S. Pat. No. 7,645,913 (Clark) describing preparing alkylaromatic compounds by liquid phase alkylation in a multistage reaction system over acidic solid oxide catalyst in the first reaction zone having more acid sites per unit volume of catalyst than the catalyst in the second reaction zone at conversion conditions including for ethylbenzene a temperature as high as 270° C. and pressure as high as 8,300 kPa, and for cumene a temperature as high as 250° C. and pressure as high as 5,000 kPa. U.S. Patent Publication No. 2008/0287720 A1 (Clark) describes alkylation of benzene over catalyst of MCM-22 family material in a reaction zone having water content maintained at from 1 to 900 wppm. U.S. Patent Publication No. 2009/0137855 A1 (Clark) describes a mixed phase process for producing alkylaromatic compounds from a dilute alkene feedstock which also includes alkane impurities. In the latter Publication, the volume ratio of liquid to vapor in the feedstock is from 0.1 to 10.

Existing alkylation processes for producing alkylaromatic compounds, for example, ethylbenzene and cumene, inherently produce polyalkylated species as well as the desired monoalkyated product. It is therefore normal to transalkylate the polyalkylated species with additional aromatic feed, for example benzene, to produce additional monoalkylated product, for example ethylbenzene or cumene, either by recycling the polyalkylated species to the alkylation reactor or, more frequently, by feeding the polyalkylated species to a separate transalkylation reactor. Examples of catalysts which have been used in the alkylation of aromatic species, such as alkylation of benzene with ethylene or propylene, and in the transalkylation of polyalkylated species, such as polyethylbenzenes and polyisopropylbenzenes, are listed in U.S. Pat. No. 5,557,024 (Cheng) and include MCM-49, MCM-22, PSH-3, SSZ-25, zeolite X, zeolite Y, zeolite Beta, acid dealuminized mordenite and TEA-mordenite. Transalkylation over a small crystal (<0.5 micron) form of TEA-mordenite is also disclosed in U.S. Pat. No. 6,984,764.

Where the alkylation step is performed in the liquid phase, it is also desirable to conduct the transalkylation step under liquid phase conditions. However, by operating at relatively low temperatures, liquid phase processes impose increased requirements on the catalyst, particularly in the transalkylation step where the bulky polyalkylated species must be converted to additional monoalkylated product without producing unwanted by-products. This has proven to be a significant problem in the case of cumene production where existing catalysts have either lacked the desired activity or have resulted in the production of significant quantities of by-products such as ethylbenzene and n-propylbenzene.

Although it is suggested in the art that catalysts for conversion of feedstock comprising an alkylatable aromatic compound and an alkylating agent to alkylaromatic conversion product under at least partial liquid phase conversion conditions are composed of a porous crystalline aluminosilicate molecular sieves having an MWW structure type, the present improved process has remained elusive. Finding a commercially acceptable catalyst for such processes conducted under at least partial liquid phase conversion conditions which increases conversion and does not significantly affect monoselectivity, i.e., lower di- or polyalkyl product make, would allow capacity expansion in existing plants and lower capital expense for grassroots plants as a result of lower aromatic compound/alkylating agent ratios. According to the present invention, it has now unexpectedly been found that a liquid phase or at least partial liquid phase alkylation process for producing alkylaromatics conducted in the presence of a specific catalyst comprising a porous crystalline material, e.g., a crystalline aluminosilicate, ("crystal"), having the structure type of FAU, *BEA or MWW, said catalyst having a Relative Activity measured as an $RA_{220}$ (hereinafter more particularly described) of at least 7.5 or at least 8.6, for example from 7.5 to 30 or from 8.6 to 12.0, or an $RA_{180}$ (hereinafter more particularly described) of at least 2.5 or at least 3.5, for example from 2.5 to 10 or from 3.5 to 6.0, yields a unique combination of activity and monoselectivity, while allowing operation at lower reaction pressures and lower alkylating agent feed supply pressures. This is especially the case when the process involves at least partial liquid phase alkylation for the manufacture of ethylbenzene or cumene. This eliminates the need for costly pressure booster compressors in the commercial plant, which is a tremendous commercial advantage.

SUMMARY OF THE INVENTION

According to the present invention, there is provided an improved process for the catalytic conversion of a feedstock comprising an alkylatable aromatic compound and an alkylating agent to form a conversion product comprising the desired alkylaromatic compound by contacting said feedstock in at least partial liquid phase under catalytic conversion conditions with a catalyst composition comprising a porous crystalline material, e.g., a crystalline aluminosilicate, having a structure type of FAU, *BEA or MWW, or a mixture thereof, said catalyst composition having a Relative Activity measured at 220° C. as an $RA_{220}$ of at least 7.5 or at least 8.6, for example from 7.5 to 30 or from 8.6 to 12.0; or measured at 180° C. as an $RA_{180}$ of at least 2.5 or at least 3.5, for example from 2.5 to 10 or from 3.5 to 6.0, allowing operation at lower reaction pressures and lower alkylating agent feed supply pressures; for example, a pressure of from about 250 psig (1724 kPa) to about 450 psig (3102 kPa), preferably from about 350 psig (2413 kPa) to about 450 psig (3102 kPa). The catalyst Relative Activity allows for 95+% conversion of alkylating agent at reaction temperature or pressure that normally require either expansion of the reactor or boosting of the alkylating agent feed pressure, wherein said Relative Activity is the percent temperature rise in an adiabatic pipe reactor having one or more thermocouples divided by the percentage bed length based on the position of said thermocouples in said reactor.

According to one aspect of the invention, there is provided a process for selectively producing a desired monoalkylated aromatic compound comprising the step of contacting an alkylatable aromatic compound with an alkylating agent in the presence of catalyst under at least partial liquid phase conditions, said catalyst comprising a porous crystalline material, e.g., a crystalline aluminosilicate, having a Relative Activity measured at 220° C. as an $RA_{220}$ of at least 7.5 or at least 8.6, for example from 7.5 to 30 or from 8.6 to 12.0; or measured at 180° C. as an $RA_{180}$ of at least 2.5 or at least 3.5, for example from 2.5 to 10 or from 3.5 to 6.0. Another aspect of the present invention is an improved alkylation process for the selective production of monoalkyl benzene comprising the step of reacting benzene with an alkylating agent such as ethylene or propylene under alkylation conditions in the presence of alkylation catalyst which comprises a porous crystalline material, e.g., a crystalline aluminosilicate, having a Relative Activity measured at 220° C. as an $RA_{220}$ of at least 7.5 or at least 8.6, for example from 7.5 to 30 or from 8.6 to 12.0; or measured at 180° C. as an $RA_{180}$ of at least 2.5 or at least 3.5, for example from 2.5 to 10 or from 3.5 to 6.0.

The catalyst for use in the present improved process comprises a porous crystalline molecular sieve having the structure type of FAU, such as faujasite, zeolite Y, Ultrastable Y (USY, described in U.S. Pat. Nos. 3,293,192 and 3,449,070), Dealuminized Y (Deal Y, preparation of which is described in U.S. Pat. No. 3,442,795), rare earth exchanged Y (REY, described in U.S. Pat. No. 4,415,438); the structure type of *BEA, such as zeolite Beta (described in U.S. Pat. No. 3,308,069); or the structure type of MWW, such as, for example, those having an X-ray diffraction pattern including d-spacing maxima at 12.4±0.25, 6.9±0.15, 3.57±0.07 and 3.42±0.07 Angstroms; or a mixture of porous crystalline molecular sieves having the structure type of FAU, *BEA or MWW. The catalyst must exhibit a Relative Activity measured at 220° C. as an $RA_{220}$ of at least 7.5 or at least 8.6, for example from 7.5 to 30 or from 8.6 to 12.0; or measured at 180° C. as an $RA_{180}$ of at least 2.5 or at least 3.5, for example from 2.5 to 10 or from 3.5 to 6.0, allowing operation at lower reaction pressures and lower alkylating agent feed supply pressures.

Molecular sieves of MWW structure type generally have an X-ray diffraction pattern including d-spacing maxima at 12.4±0.25, 6.9±0.15, 3.57±0.07 and 3.42±0.07 Angstroms. The X-ray diffraction data used to characterize the material are obtained by standard techniques using the K-alpha doublet of copper as the incident radiation and a diffractometer equipped with a scintillation counter and associated computer as the collection system. Molecular sieves of MWW structure type include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), ITQ-30 (described in International Patent Publication No. WO2005/118476), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and UZM-8HS (described in U.S. Pat. No. 7,713,513). Preferably, the molecular sieve for the catalyst herein is selected from MCM-22, MCM-36, MCM-49, MCM-56 and isotypes of MCM-49 and MCM-56, such as ITQ-2 and ITQ-30.

DETAILED DESCRIPTION OF THE INVENTION

The present invention relates to an improved process for production of monoalkylated aromatic compounds, particularly ethylbenzene and cumene, by the liquid or partial liquid phase alkylation of an alkylatable aromatic compound, particularly benzene. More particularly, the present process uses a catalyst composition comprising faujasite, zeolite Y, zeolite Beta, or a porous crystalline material of the MWW structure type, e.g., MCM-22, MCM-36, MCM-49, MCM-56, ITQ-1, ITQ-2 or ITQ-30, having a Relative Activity measured at 220° C. as an $RA_{220}$ of at least 7.5 or at least 8.6, for example from 7.5 to 30 or from 8.6 to 12.0; or measured at 180° C. as an $RA_{180}$ of at least 2.5 or at least 3.5, for example from 2.5 to 10 or from 3.5 to 6.0, allowing operation at lower reaction pressures, e.g., a reactor outlet pressure of about 450 psig (3102 kPa) or less, and lower alkylating agent, e.g., ethylene or propylene, feed supply pressure of 450 psig (3102 kPa) or less, e.g., 400 psig (2758 kPa) or less. The term "liquid or partial liquid phase" in reference to the present improved process means that the reaction mixture comprises greater than 10 volume % liquid, for example greater than 30 volume % liquid, up to 100 volume % liquid.

Methods for producing the catalysts required for use in the present invention comprise those taught in the Publications listed herein and incorporated herein by reference, modified only by adjustments designed to insure the final catalyst to have a Relative Activity measured as an $RA_{220}$ of at least 7.5 or at least 8.6, for example from 7.5 to 30 or from 8.6 to 12.0; or $RA_{180}$ of at least 2.5 or at least 3.5, for example from 2.5 to 10 or from 3.5 to 6.0. This is well within the ability of those skilled in catalyst manufacturing art. For example, U.S. Pat. No. 4,954,325 describes crystalline MCM-22 and catalyst comprising same, U.S. Pat. No. 5,236,575 describes crystalline MCM-49 and catalyst comprising same, and U.S. Pat. No. 5,362,697 describes crystalline MCM-56 and catalyst comprising same.

One method for modifying the Relative Activity of the final catalyst is to adjust the zeolite content of the final catalyst, in which an increased zeolite content results in a higher Relative Activity, and a decreased zeolite content results in a lower Relative Activity.

Another method for modifying the Relative Activity of the final catalyst is by streaming U.S. Pat. Nos. 4,663,492; 4,594,146; 4,522,929; and 4,429,176, the entire disclosures of which are incorporated herein by reference, describe conditions for the steam stabilization of zeolite catalysts which can be utilized to steam-stabilize the catalyst for use herein. The steam stabilization conditions include contacting the final catalyst with, e.g., 5-100% steam at a temperature of at least about 300° C. (e.g., 300-650° C.) for at least one hour (e.g., 1-200 hours) at a pressure of 101-2,500 kPa. In a more particular embodiment, the final catalyst can be made to undergo steaming with 75-100% steam at 315° C.-500° C. and atmospheric pressure for 2-25 hours. In accordance with the steam stabilization treatment described in the above-mentioned patents, the steaming of the catalyst can take place under conditions sufficient to initially increase the Alpha Value of the catalyst, and produce a steamed final catalyst having a peak Alpha Value. If desired, steaming can be continued to subsequently reduce the Alpha Value from the peak Alpha Value to an Alpha Value which is substantially the same as the Alpha Value of the unsteamed final catalyst.

The Alpha Value is an approximate indication of the catalytic cracking activity of the final catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant=0.016 $sec^{-1}$). The Alpha Test is described in U.S. Pat. No. 3,354,078, and in the Journal of Catalysis, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C., and a variable flow rate as described in detail in the Journal of Catalysis, Vol. 61, p. 395.

In adjusting the method to form the catalyst required for use herein, care is taken to do so such that the final catalyst product has a Relative Activity measured at 220° C. as an $RA_{220}$ of at least 7.5 or at least 8.6, for example from 7.5 to 30 or from 8.6 to 12.0; or measured at 180° C. as an $RA_{180}$ of at least 2.5 or at least 3.5, for example from 2.5 to 10 or from 3.5 to 6.0.

The term "aromatic" in reference to the alkylatable aromatic compounds which may be useful as a feedstock herein is to be understood in accordance with its art-recognized scope. This includes alkyl-substituted and unsubstituted mono- and polynuclear compounds. Compounds of an aromatic character that possess a heteroatom are also useful provided they do not act as catalyst poisons under the reaction conditions selected.

Substituted aromatic compounds that can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups that do not interfere with the alkylation reaction.

Suitable aromatic compounds include benzene, naphthalene, anthracene, naphthacene, perylene, coronene, and phenanthrene, with benzene being preferred.

Generally the alkyl groups that can be present as substituents on the aromatic compound contain from 1 to about 22 carbon atoms and usually from about 1 to 8 carbon atoms, and most usually from about 1 to 4 carbon atoms.

Suitable alkyl substituted aromatic compounds include toluene, xylene, isopropylbenzene, n-propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic compounds can also be used as starting materials and include aromatic organics such as are produced by the alkylation of aromatic organics with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$. When cumene or ethylbenzene is the desired product, the present process produces acceptably little by-products such as xylenes. The xylenes made in such instances may be less than about 500 ppm.

Reformate containing a mixture of benzene, toluene and/or xylene constitutes a useful feed for the alkylation process of this invention.

The alkylating agents that may be useful in the process of this invention include olefins such as ethylene and propylene; alcohols (inclusive of monoalcohols, dialcohols, trialcohols, etc.) such as methanol, ethanol and the propanols; aldehydes such as formaldehyde, acetaldehyde and propionaldehyde;

and alkyl halides such as methyl chloride, ethyl chloride and the propyl chlorides, and so forth.

Mixtures of light olefins are useful as alkylating agents in the alkylation process of this invention. Accordingly, mixtures of ethylene and propylene which are major constituents of a variety of refinery streams, e.g., fuel gas, gas plant off-gas containing ethylene, propylene, etc., naphtha cracker off-gas containing light olefins, refinery FCC propane/propylene streams, etc., are useful alkylating agents herein. For example, a typical FCC light olefin stream possesses the following composition:

|           | Wt. % | Mole % |
|-----------|-------|--------|
| Ethane    | 3.3   | 5.1    |
| Ethylene  | 0.7   | 1.2    |
| Propane   | 4.5   | 15.3   |
| Propylene | 42.5  | 46.8   |
| Isobutane | 12.9  | 10.3   |
| n-Butane  | 3.3   | 2.6    |
| Butenes   | 22.1  | 18.32  |
| Pentanes  | 0.7   | 0.4    |

Non-limiting examples of reaction products that may be obtained from the process of the present invention include ethylbenzene from the reaction of benzene with ethylene, cumene from the reaction of benzene with propylene, ethyltoluene from the reaction of toluene with ethylene, and cymenes from the reaction of toluene with propylene. Particularly preferred process mechanisms of the invention relate to the production of cumene by the alkylation of benzene with propylene, and production of ethylbenzene by the alkylation of benzene with ethylene.

The reactants for the present improved process can be in partially or completely liquid phase and can be neat, i.e., free from intentional admixture or dilution with other material, or they can be brought into contact with the required catalyst composition with the aid of carrier gases or diluents such as, for example, hydrogen or nitrogen.

The improved alkylation process of this invention may be conducted such that the reactants, i.e., the alkylatable aromatic compound and the alkylating agent, are brought into contact with the present catalyst in a suitable reaction zone such as, for example, in a flow reactor containing a fixed bed of the catalyst composition, under effective alkylation conditions. Such conditions include a temperature of less than about 270° C., from about 150° C. to less than about 270° C., preferably from about 160° C. to less than about 270° C., a pressure of from about 250 psig (1724 kPa) to about 450 psig (3102 kPa), preferably from about 350 psig (2413 kPa) to about 450 psig (3102 kPa), a molar ratio of alkylatable aromatic compound to alkylating agent of from about 0.1:1 to about 100:1, preferably from about 0.5:1 to about 30:1, and a feed weight hourly space velocity (WHSV) based on the alkylating agent of from about 0.1 to 100 $hr^{-1}$, preferably from about 0.5 to about 50 $hr^{-1}$.

When benzene is alkylated with ethylene to produce ethylbenzene, the alkylation reaction is preferably carried out in the liquid phase under conditions including a temperature of from about 150° C. to less than about 270° C., more preferably from about 165° C. to less than about 270° C.; a pressure up to about 450 psig (3102 kPa), preferably from about 300 psig (2068 kPa) to about 450 psig (3102 kPa); a weight hourly space velocity (WHSV) based on the ethylene alkylating agent of from about 0.1 to about 20 $hr^{-1}$, more preferably from about 0.5 to about 6 $hr^{-1}$; and a molar ratio of benzene to ethylene in the alkylation reactor of from about 0.5:1 to about 100:1 molar, more preferably from about 1:1 to about 30:1 molar.

When benzene is alkylated with propylene to produce cumene, the reaction may also take place under liquid phase conditions including a temperature of less than about 200° C., preferably from about 100 to 200° C.; a pressure of about 450 psig (3102 kPa) or less, e.g., from about 250 psig (1724 kPa) to about 600 psig (4137 kPa) or less; or about 450 psig (3102 kPa); a weight hourly space velocity (WHSV) based on propylene alkylating agent of from about 0.1 $hr^{-1}$ to about 25 $hr^{-1}$, preferably from about 0.3 $hr^{-1}$ to about 5 $hr^{-1}$; and a molar ratio of benzene to propylene in the alkylation reactor of from about 0.5:1 to about 50:1 molar, more preferably from about 1:1 to about 20:1 molar.

The catalyst required for use in the present invention comprises a crystalline molecular sieve having the structure of zeolite Y, Beta or one having an MWW structure type such as, for example, those having an X-ray diffraction pattern including d-spacing maxima at 12.4±0.25, 6.9±0.15, 3.57±0.07 and 3.42±0.07 Angstroms. Examples of MWW structure type materials include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in U.S. Pat. No. 6,231,751), ITQ-30 (described in WO 2005/118476), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and UZM-8HS (described in U.S. Pat. No. 7,713,513). The catalyst must have a Relative Activity measured at 220° C. as an $RA_{220}$ of at least 7.5 or at least 8.6, for example from 7.5 to 30 or from 8.6 to 12.0; or measured at 180° C. as $RA_{180}$ of at least 2.5 or at least 3.5, for example from 2.5 to 10 or from 3.5 to 6.0.

In addition to, and upstream of, the reaction zones, a by-passable reactive or unreactive guard bed may normally be located in a reactor separate from the alkylation reactor. Such guard bed may also be loaded with an alkylation or transalkylation catalyst, which may be the same or different from the catalyst used in the reaction zone(s). Such guard bed is maintained from under ambient conditions, or at suitable alkylation or transalkylation conditions. At least a portion of alkylatable aromatic compound, and optionally at least a portion of the alkylating agent, are passed through the unreactive or reactive guard bed prior to entry into the reaction zone. These guard beds not only serve to affect the desired alkylation reaction, but is also used to remove any reactive impurities in the feeds, such as nitrogen compounds, which could otherwise poison the remainder of the alkylation or transalkylation catalyst. The catalyst in the reactive or unreactive guard bed is therefore subject to more frequent regeneration and/or replacement than the remainder of the alkylation or transalkylation catalyst, and hence the guard bed is typically provided with a by-pass circuit so that the alkylation feed(s) may be fed directly to the series connected reaction zones in the reactor while the guard bed is out of service. The reactive or unreactive guard bed may be operated in co-current upflow or downflow operation. One example of an aromatics alkylation system including a reactive guard bed is disclosed in U.S. Pat. No. 6,995,295, the entire contents of which are incorporated herein by reference.

In the reaction mechanism of the present invention, the alkylation reactor effluent may contain excess aromatic feed, monoalkylated product, polyalkylated products, and various impurities. The aromatic feed is recovered by distillation and recycled to the alkylation reactor. Usually a small bleed is taken from the recycle stream to eliminate unreactive impurities from the loop. The bottoms from the distillation may be further distilled to separate monoalkylated product from polyalkylated products and other heavies.

The polyalkylated products separated from the alkylation reactor effluent may be reacted with additional aromatic feed in a transalkylation reactor, separate from the alkylation reactor, over a suitable transalkylation catalyst. The transalkylation catalyst may comprise one or a mixture of crystalline molecular sieves having the structure type of FAU, *BEA or MWW, or a mixture thereof. Such MWW structure type having an X-ray diffraction pattern including d-spacing maxima at 12.4±0.25, 6.9±0.15, 3.57±0.07 and 3.42±0.07 Angstroms.

The X-ray diffraction data used to characterize said above catalyst structure types are obtained by standard techniques using the K-alpha doublet of copper as the incident radiation and a diffractometer equipped with a scintillation counter and associated computer as the collection system. Materials having the above X-ray diffraction lines include, for example, MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in U.S. Pat. No. 6,231,751), ITQ-30 (described in WO 2005/118476), MCM-36 (described in U.S. Pat. No. 5,250,277), MCM-49 (described in U.S. Pat. No. 5,236,575), and MCM-56 (described in U.S. Pat. No. 5,362,697).

Zeolite Beta is disclosed in U.S. Pat. No. 3,308,069. Zeolite Y occurs naturally (e.g., as in faujasite), but may also be used in one of its synthetic forms, such as Ultrastable Y (USY), which is disclosed in U.S. Pat. No. 3,449,070, and rare earth exchanged Y (REY), which is disclosed in U.S. Pat. No. 4,415,438.

The catalyst for use in the present invention must have a Relative Activity measured as an $RA_{220}$ of at least 7.5 or at least 8.6, for example from 7.5 to 30 or from 8.6 to 12.0; or an $RA_{180}$ of at least 2.5 or at least 3.5, for example from 2.5 to 10 or from 3.5 to 6.0, allowing operation at lower reaction pressures, e.g., a reactor outlet pressure of about 450 psig (3102 kPa) or less, and lower alkylating agent, e.g., ethylene or propylene, feed supply pressure of 450 psig (3102 kPa) or less, e.g., 400 psig (2758 kPa) or less. The Relative Activity measured as $RA_{220}$ or $RA_{180}$ is determined by a method similar to that described by S. Folger in *Elements of Chemical Reactor Engineering*, $2^{nd}$ Edition, pages 406-407. In this method using an adiabatic reactor, an energy balance is used to relate the temperature rise to the conversion of ethylene. With thermocouple positions, inlet temperature, pressure and conversions known, the Relative Activity of the catalyst may be determined using a differential reactor analysis. For this analysis, the Relative Activity is calculated by the percent temperature rise in an adiabatic reactor having one or more thermocouples divided by the percentage of the bed length based on the position of said thermocouple in said reactor. In short, Relative Activity (RA)=ΔT/L, wherein ΔT is percent temperature rise and L is percentage of the bed length. When the inlet temperature to the adiabatic reactor is 180° C., the value of RA is $RA_{180}$. When the inlet temperature to the adiabatic reactor is 220° C., the value of RA is $RA_{220}$.

This RA determination is exemplified by the following experiments in which an adiabatic 0.75 inch (1.9 cm) diameter pipe reactor with multipoint thermocouples is loaded with approximately 28 grams of a specified catalyst. The catalyst composition is tightly packed between inert alumina beds to provide good flow distribution. A feed comprising ethylene and benzene (1:1.5 molar), heated to an inlet temperature of 180° C. or 220° C., passes through the bed of the catalyst composition enabling reaction and exits the reactor as effluent. A part of the effluent is recycled back to the feed in order to maintain an adiabatic temperature rise of approximately 40° C. The recycle to feed (weight) ratio is maintained at 6 to 1 to maintain liquid phase conditions. The multipoint thermocouple in the bed consists of six thermocouples that are used to measure the temperature at 6 points inside the bed. Results are described in Table 1 with a catalyst composition of Catalyst A and Catalyst B being the same MWW structure type material having an X-ray diffraction pattern including d-spacing maxima at 12.4±0.25, 6.9±0.15, 3.57±0.07 and 3.42±0.07 Angstroms, except that Catalyst A and Catalyst B have differing zeolite/binder weight ratios. Catalyst A has a zeolite/binder ratio of 80/20 by weight. Catalyst B has a zeolite/binder ratio of 60/40 by weight.

TABLE 1

| Catalyst | Inlet Temperature (° C.) | Thermocouple Position (Percent of Bed Length) | Percent Temperature Rise | RA |
|---|---|---|---|---|
| B (Lower Activity) | 180 | 4.9% | 9.0% | 1.8 |
| B (Lower Activity) | 220 | 4.9% | 32% | 6.5 |
| A (Higher Activity) | 180 | 4.4% | 23% | 5.2 |
| A (Higher Activity) | 220 | 4.4% | 47% | 10.7 |

The catalyst composition for use in the present invention may include an inorganic oxide material matrix or binder. Such matrix or binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the inorganic oxide material include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

Specific useful catalyst matrix or binder materials for the catalyst composition employed herein include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used.

For the improvement of the present invention, relative proportions of the crystalline molecular sieve and binder or matrix are not critical, so long as the catalyst has a Relative Activity measured at 220° C. as an $RA_{220}$ of at least 7.5 or at least 8.6, for example from 7.5 to 30 or from 8.6 to 12.0; or measured at 180° C. as an $RA_{180}$ of at least 2.5 or at least 3.5, for example from 2.5 to 10 or from 3.5 to 6.0.

The catalyst composition for use in the present invention, or its crystalline molecular sieve component, may or may not contain added functionalization, such as, for example, a metal of Group VI (e.g., Cr and Mo), Group VII (e.g., Mn and Re) or Group VIII (e.g., Co, Ni, Pd and Pt), or phosphorus.

Non-limiting prophetic examples of the invention involving an improved alkylation mechanism are described with reference to the following experiments. In these experiments, Catalyst A and B, referenced above, are MWW structure type materials having an X-ray diffraction pattern including d-spacing maxima at 12.4±0.25, 6.9±0.15, 3.57±0.07 and 3.42±0.07 Angstroms.

EXAMPLES

Example 1

Exemplifying current commercial operation with high pressure ethylene feed, to a reaction vessel containing a bed of Catalyst B having an $RA_{220}$ of 6.2 is fed benzene and ethylene in the molar ratio of benzene to ethylene of about 15:1. The ethylene feed pressure is 600 psig (4137 kPa), the outlet pressure of the reaction vessel is maintained at 500 psig (3447 kPa) and the reactor temperature is 220° C. Complete conversion exceeding 99.99% of the ethylene is achieved.

Example 2

In a comparative example, an ethylene feedstock at lower pressure of 450 psig (3102 kPa) is selected. In order to operate the reactor, the outlet pressure of the reactor must be reduced to 370 psig (2551 kPa) to maintain liquid phase. As an alternative option, an ethylene compressor is selected to be installed to raise the pressure of the ethylene feedstock up to 600 psig (4137 kPa) and operate the same catalyst as in Example 1 with an $RA_{220}$ of 6.2. Other reaction conditions of Example 1 are maintained in this experiment. The installed cost of the compressor exceeds two million dollars. At the same benzene to ethylene molar ratio as Example 1 and with the same catalyst and conditions, the production rate is the same.

Example 3

As in Example 2, an ethylene feedstock at lower pressure of 450 psig (3102 kPa) is selected. The outlet pressure of the reactor must be reduced to 370 psig (2551 kPa) to maintain liquid phase. The reaction temperature is lowered to 180° C. to enable liquid phase operation at the same benzene to ethylene molar ratio as in Example 2. The same catalyst as in Example 1 and 2 is used, but the need for an expensive ethylene compressor is eliminated. Because the Catalyst B activity $RA_{180}$ of 1.8 is lower than required at these conditions, conversion of ethylene is lower than 99.99%, and incomplete. To achieve complete ethylene conversion, the amount of ethylene fed is reduced, which leads to an overall loss of production, or the catalyst quantity is increased significantly to maintain production.

Example 4

Exemplifying the present improved process, the scenario described in Example 3 is modified by the substitution of Catalyst A having an $RA_{180}$ of 5.2. At 370 psig (2551 kPa) and 180° C., the operation remains in liquid phase. An ethylene conversion exceeding 99.99% is achieved without the expensive ethylene compressor required in Example 2. The use of a higher activity Catalyst A has enabled the use of a lower pressure ethylene feedstock without requiring new equipment to be installed.

All patents, patent applications, test procedures, priority documents, articles, Publications, manuals, and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

While the illustrative embodiments of the invention have been described with particularity, it will be understood that various other modifications will be apparent to and may be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

We claim:

1. In a process for catalytic conversion of a feedstock comprising at least one alkylatable aromatic compound comprising benzene and an alkylating agent comprising ethylene or propylene to form a conversion product comprising an alkylaromatic compound, the process comprising the step of contacting said feedstock in at least partial liquid phase under catalytic conversion conditions including a reactor outlet pressure and an alkylating agent feed supply pressure, with a catalyst composition comprising a porous crystalline material having a MWW structure selected from the group consisting of MCM-22, MCM-36, MCM-49, MCM-56, ITQ-1, ITQ-2, ITQ-30, PSH-3, SSZ-25, ERB-1, UZM-8, UZM-8HS and mixtures thereof, the improvement comprising the steps of:

(a) modifying said catalyst composition to have a Relative Activity measured as an $RA_{220}$ at 220° C. of 8.6 to 12.0 or $RA_{180}$ at 180° C. of from 3.5 to 6.0 by:
 (i) increasing the zeolite content of said catalyst composition or steaming the catalyst composition to increase the Alpha Value, or
 (ii) decreasing the zeolite content of said catalyst composition or steaming the catalyst composition to decrease the Alpha Value; and (b) lowering said reactor pressure to about 370 psig (3102 kPa) or less or said alkylating agent feed supply pressure from about 370 psig (3102 kPa) or less, wherein said Relative Activity is the percent temperature rise in an adiabatic pipe reactor having one or more thermocouples divided by the percentage bed length based on the position of said thermocouples in said reactor.

2. The process of claim 1, wherein said conversion conditions include said molar ratio of alkylatable aromatic compound to alkylating agent of from about 0.5:1 to about 10:1, and said feed weight hourly space velocity (WHSV) based on the alkylating agent of from about 0.1 to about 50 $hr^{-1}$.

3. The process of claim 1, when said alkylatable aromatic compound comprises benzene, and said alkylating agent comprises ethylene, said alkylaromatic compound comprises ethylbenzene.

4. The process of claim 1, when said alkylatable aromatic compound comprises benzene, and said alkylating agent comprises propylene, said alkylaromatic compound comprises cumene.

* * * * *